(12) United States Patent
Chang et al.

(10) Patent No.: US 9,498,497 B2
(45) Date of Patent: Nov. 22, 2016

(54) METHOD OF TREATING LUNG DISEASES USING CELLS SEPARATED OR PROLIFERATED FROM UMBILICAL CORD BLOOD

(75) Inventors: Yun Sil Chang, Seoul (KR); Won Soon Park, Seongnam-si (KR); Yoon-Sun Yang, Seoul (KR)

(73) Assignees: MEDIPOST Co., Ltd., Seongnam-si, Gyeonggi-do (KR); Samsung Life Public Welfare Foundation, Seoul (KR)

( * ) Notice: Subject to any disclaimer, the term of this patent is extended or adjusted under 35 U.S.C. 154(b) by 365 days.

(21) Appl. No.: 12/184,695

(22) Filed: Aug. 1, 2008

(65) Prior Publication Data

US 2008/0311088 A1    Dec. 18, 2008

Related U.S. Application Data

(63) Continuation-in-part of application No. PCT/KR2007/000535, filed on Jan. 31, 2007, which is a continuation-in-part of application No. 11/425,949, filed on Jun. 22, 2006, now abandoned.

(30) Foreign Application Priority Data

Feb. 1, 2006   (KR) .................. 10-2006-0009625
Jul. 31, 2006  (WO) ............... PCT/KR2006/003009

(51) Int. Cl.
*A61K 35/12*   (2015.01)
*A61K 35/28*   (2015.01)
*A61K 35/51*   (2015.01)
*A61K 45/06*   (2006.01)
*A61K 35/16*   (2015.01)

(52) U.S. Cl.
CPC .............. *A61K 35/28* (2013.01); *A61K 35/16* (2013.01); *A61K 35/51* (2013.01); *A61K 45/06* (2013.01)

(58) Field of Classification Search
CPC ...... A61K 35/28; A61K 35/51; A61K 35/16; A61K 35/17
See application file for complete search history.

(56) References Cited

U.S. PATENT DOCUMENTS

| | | | |
|---|---|---|---|
| 6,461,645 B1 | 10/2002 | Boyse et al. | |
| 2004/0151703 A1 | 8/2004 | Ha et al. | |
| 2004/0180040 A1* | 9/2004 | Phillips et al. | 424/93.7 |
| 2004/0219136 A1* | 11/2004 | Hariri | 424/93.71 |
| 2005/0019908 A1 | 1/2005 | Hariri | |
| 2005/0239897 A1* | 10/2005 | Pittenger et al. | 514/569 |
| 2005/0277576 A1* | 12/2005 | Franco | 514/2 |
| 2006/0159666 A1* | 7/2006 | Willing et al. | 424/93.7 |
| 2007/0178073 A1 | 8/2007 | Chang et al. | |

FOREIGN PATENT DOCUMENTS

| | | |
|---|---|---|
| KR | 1020030015160 | 2/2003 |
| KR | 1020030015160 A | 2/2003 |
| WO | 03/070922 A1 | 8/2003 |
| WO | WO-03078567 A2 | 9/2003 |
| WO | WO-2004071283 A2 | 8/2004 |
| WO | 2005/001072 A1 | 1/2005 |
| WO | WO-2005093044 A1 | 10/2005 |
| WO | 2007089063 A1 | 2/2006 |
| WO | 2007089102 A1 | 1/2007 |
| WO | WO 2007/124594 | 11/2007 |

OTHER PUBLICATIONS

Lee et al., "Isolation of Mesenchymal Stem Cells from Cryopreserved Human Umbilical Cord Blood", Int J Hematol , 2005, vol. 81, pp. 126-130.*
Lee et al., "Isolation of multipotent mesenchymal stem cells from umbilical cord blood", Blood,2004, vol. 103, No. 6, pp. 1669-1675.*
Panepucci et al., "Comparison of Gene Expression of Umbilical Cord Vein and Bone Marrow-Derived Mesenchymal Stem Cells", Stem Cells, 2004, vol. 22, pp. 1263-1278.*
Gupta et al., "Intrapulmonary Administration of Mesenchymal Stem Cells Reduces Endotoxin-Induced Acute Lung Injury and Mortality in a Mouse Model", Journal of Investigative Medicine, Jan. 2006, vol. 54, Issue 1, p. s112.*
Wang et al., "Adult stem cells from bone marrow stroma differentiate into airway epithelial cells: Potential therapy for cystic fibrosis", PNAS, Jan. 4, 2005, vol. 102, No. 1, pp. 186-191.*
U.S. Appl. No. 60/447,252, filed Nov. 4, 2004, Hariri.
"S. Korean Researchers Test Adult Stem Cells to Treat Lung Cancer," Stem Cell News (www.stemcellnews.com), Jan. 31, 2006.
Rojas, M., et al., "Bone Marrow-Derived Mesenchymal Stem Cells in Repair of the Injured Lung," Am. J. Respir. Cell Mol. Biol., Aug. 2005, 33(2), pp. 145-152.
Ortiz, L.A., et al., "Mesenchymal stem cell engraftment in lung is enhanced bleomycin exposure and ameliorates its fibrotic effects," Proc. Natl. Acad. Sci. USA, Jul. 8, 2003, 100(14), pp. 8407-8411.
Erices, et al., "Mesenchymal Progenitor Cells in Human Umbilical Cord Blood," Br. J. Haematol, (2000) 109:235-242.
Lee, et al., "Isolation of Multipotent Mesenchymal STem Cells from Umbilical Cord Blood," Blood (Mar. 1, 2004), 103(5): 1669-1675.
Theise, et al., "Radiation Pneumonitis in Mice: A Severe Injury Model for Pneumocyte Engraftment from Bone Marrow," Exp. Hematol. 30(11):1333-1338, 2002.
Spencer & Jaffe, Journal of the Royal Society of Medicine, 2004, vol. 97, Supplemental No. 44, p. 52-56.
Wagner et al., "Comparative Characteristics of Mesenchymal Stem Cells from Human Bone Marrow, Adipose Tissue, and Umbilical Cord Blood," Exp. Hematol., Nov. 2005, 33(11), pp. 1402-1416.

(Continued)

*Primary Examiner* — Laura Schuberg
(74) *Attorney, Agent, or Firm* — Sterne, Kessler, Goldstein & Fox P.L.L.C.

(57) ABSTRACT

There is provided a method of treating lung diseases including administering cells separated or proliferated from umbilical cord blood to a patient suffering from such diseases.

2 Claims, 10 Drawing Sheets
(3 of 10 Drawing Sheet(s) Filed in Color)

(56) References Cited

OTHER PUBLICATIONS

Kotton et al., "Bone Marrow-Derived Cells as Progenitors of Lung Alveolar Epithelium," Developmental 128, 2001, pp. 5181-5188.

Suratt et al., "Human Pulmonary Chimerism After Hematopoietic Stem Cell Transplantation," American Journal of Respiratory and Critical Care Medicine, 2003, vol. 168, pp. 318-322.

Kleeberger et al., "Increased Chimerism of Bronchial and Alveolar Epithelium in Human Lung Allografts Undergoing Chronic Injury," American Journal of Pathology, 2003, vol. 162, No. 5, pp. 1487-1494.

Japanese Office Action issued Nov. 1, 2011, in Japanese application No. 2008-553140 (in Japanese).

Shinozaki et al., "The Articles of the 104th Conference of the Japan Pediatric Society," p. 284, PI093 (2001) (in Japanese).

Abe et al., "Regeneration of the Lung Cell," The Latest Medicine, Sep. 10, 2005, vol. 60, No. 9, pp. 1929-1934 (Partial English-language translation).

International Search Report mailed May 4, 2007, in PCT International Application No. PCT/KR2007/000535, filed Jan. 31, 2007.

International Search Report mailed Oct. 16, 2006, In PCT International Application No. PCT/KR2006/003009, filed Jul. 31, 2006.

International Preliminary Report on Patentability issued Aug. 5, 2008, in PCT International Application No. PCT/KR2007/000535, filed Jan. 31, 2007.

International Preliminary Report on Patentability issued Aug. 5, 2008, in PCT International Application No. PCT/KR2006/003009, filed Jul. 31, 2006.

Office Action dated Jun. 28, 2007, in U.S. Appl. No. 11/425,949.

Erices et al. (2000) "Mesenchymal Progenitor Cells in Human Umbilical Cord Blood," *Br. J. Haematol.* 109:235-242.

Lee et al. (Mar. 1, 2004) "Isolation of Multipotent Mesenchymal Stem Cells from Umbilical Cord Blood," *Blood* 103(5):1669-1675.

Ortiz et al. (Jul. 8, 2003) "Mesenchymal Stem Cell Engraftment in Lung is Enhanced in Response to Bleomycin Exposure and Ameliorates its Fibrotic Effects," *Proc. Nat Acad. Sci. USA* 100(14):8407-8411.

Theise et al. (Nov. 2002) "Radiation Pneumonitis in Mice: A Severe Injury Model for Pneumocyte Engraftment from Bone Marrow," *Exp. Hematol.* 30(11):1333-1338.

\* cited by examiner (NC)

(HC)

(HT)

(HP)

NC (a)

HC (b)

BT (c)

HT (d)

METHOD OF TREATING LUNG DISEASES USING CELLS SEPARATED OR PROLIFERATED FROM UMBILICAL CORD BLOOD

CROSS-REFERENCE TO RELATED APPLICATIONS

This application is a continuation-in-part application of International Application PCT/KR2007/000535, filed Jan. 31, 2007, which is a continuation-in-part of U.S. application Ser. No. 11/425,949, filed Jun. 22, 2006, now abandoned.

FIELD OF THE INVENTION

The present invention relates to a method of treating lung diseases, especially developmental and/or chronic lung diseases, using cells separated or proliferated from umbilical cord blood.

BACKGROUND OF THE INVENTION

Developmental and/or chronic lung diseases include adult chronic obstructive lung disease (COPD) such as cystic fibrosis and emphysema, and bronchopulmonary dysplasia of infant or premature baby. The seriousness of these diseases is that there are no effective prevention and treatment methods for these diseases in spite of the severeness and chronicity thereof.

For example, the bronchopulmonary dysplasia is a chronic lung disease induced by respiratory failure in newborn- or premature babies kept in a ventilator. Recent data for treating premature babies show an increase in the incidence of said untreatable diseases (Avery M E et al., *Pediatrics* 79:26-30, 1987). Not only the disease is a major cause of death of newborn infants, particularly, premature babies, but also surviving babies have to be hospitalized for a long period of time and serious side effects such as pulmonary hypertension must be dealt with. Even after discharge from the hospital, the rate of re-hospitalization of infants suffering from bronchopulmonary dysplasia is usually more than 50% because of their bronchopulmonary dysplasia due to their susceptibility to viral acute bronchiolitis and pneumonia. It is also known that bronchopulmonary dysplasia may progress to bronchial asthma because of continuous bronchial hyper-sensitivity (Coalson J J. *Semin Neonatol,* 8:73-81, 2003), and is further associated with a serious neurodevelopmental sequela such as cerebral palsy (Bregman J and Farrell E E, *Clin Perinatol,* 19:673-94, 1992).

An effective treatment method for bronchopulmonary dysplasia as well as other chronic lung disease of adults has not yet been developed. Studies have been focused on an approach for the treatment of bronchopulmonary dysplasia to reduce barotrauma and volutrauma caused by positive pressure ventilation or reduce oxygen concentration during the artificial ventilation treatment of newborn- and premature babies, besides the fact that steroids have been used to prevent and treat inflammation of the damaged lung. However, steroid treatment is now limited due to the recent reports suggesting that the use of steroid are associated with later abnormal neurodevelopmental prognosis, especially with the increase in cerebral palsy (Committee on Fetus and Newborn, *Pediatrics,* 109:330-8, 2002).

Recently anticipation has been rising for the treatment using stem cells having a potential to be differentiated into every organs. However, the transplantation of embryonic stem cells, which have excellent differentiation potential, has serious developmental problems caused by the generation of uncontrollable teratoma or genomic imprinting as well as ethical problems. Therefore, the application of embryonic stem cells has become limited, and instead, adult stem cells have recently attracted much interest for the treatment thereof.

Among adult stem cells, the stem cells of hematopoietic system have received much attention. The bone marrow-derived stem cells as a source for stem cells of hematopoietic system are generally grouped into two: hematopoietic stem cells and mesenchymal stem cells.

It has been known that the hematopoietic stem cells in bone marrow have plasticity, suggesting that they are differentiated into not only cells of hematopoietic system but also other various organ cells (Gussoni E et al. *Nature.,* 401:390-394, 1999; Petersen B E et al., *Science,* 284:1168-1170, 1999; Mezey E et al., *Science,* 290:1779-1782, 2000; and Krause D S et al., *Cell.,* 105:369-377, 2001). However, it is though not very common so that there is a doubt of biological usefulness. Some reports suggest that such phenomena might result from cell fusion (Wagers A J et al., *Science,* 297:2256-2259, 2002).

On the other hand, mesenchymal stem cells separated from bone marrow of adult mice, named 'multipotent adult progenitor cells (MAPC)', are capable of differentiating into all three germ layers of ectoderm, mesoderm and endoderm, and in fact they have proven to differentiate into almost all organ cells when injected into the blastocyst of a mouse. These cells were reported to have embryonic stem cell markers such as OCT-4, Rex-1 and SSEA-1 (Jiang Y et al., *Nature,* 418:41-49, 2002).

It has been much noted that similar stem cells separated from human bone marrow can be used for cell therapy for various diseases and damages (Reyes M et al., *Blood,* 98:2615-2625,2001; and Woodbury D et al., *J Neurosci Res.,* 61:364-370, 2000). However, the numbers of hematopoietic stem cells and mesenchymal stem cells in bone marrow decrease with aging (Geiger H et al., *Nat Immunol.,* 3:329-333, 2002), besides the problem that bone marrow extraction is distressing to the patient, which limits the actual clinical application. Thus, alternatives have been searched.

Umbilical cord is the line connecting a mother and the fetus through which nutrition is provided and wastes are excreted, and the blood inside thereof is so-called umbilical cord blood. The umbilical cord blood seems to be the most appropriate alternative of bone marrow in extracting the stem cells of hematopoietic system because it contains more primitive stem cells than those of bone marrow. In addition, such cell extraction is much easier.

The transplantation of hematopoietic stem cells extracted from umbilical cord blood has been clinically applied since 1980s, because of their advantages over bone marrow: higher hematopoietic proliferation activity which means more hematopoietic stem cells present per unit volume (Szilvassy S J et al., *Blood,* 98:2108-2115, 2001); less HLA (human leukocyte antigen) incompatibility which means less graft versus host reactions (Rocha V et al., *N Engl J Med.,* 342:1846-1854, 2000); easier and less invasive extraction (Rubinstein P et al., *N Engl J Med.,* 339:1565-1577, 1998); and remarkably lower risks compared to those which may be caused by autologous bone marrow transplantation in case of various types of cancer or other diseases. In particular, umbilical cord blood bank has recently been in operation to provide services of preservation and amplification of umbilical cord blood, which has triggered various clinical practices for transplantation of hematopoietic stem cells of umbilical cord blood.

The question has not been settled and public attention has been directed as to whether the mesenchymal stem cells, particularly, MAPC-like cells having excellent differentiation potential into various organ cells are present in umbilical cord blood. This is because it would be a break-through discovery in cell therapy, and cell and tissue regenerative medicine, if mass-production of such mesenchymal stem cells or MAPC-like cells from umbilical cord blood can be achieved. It has been predicted based on the primitiveness of stem cells of umbilical cord blood that MAPC-like cells exist more in umbilical cord blood than in the bone marrow. Recently, mesenchymal stem cells were found present in the umbilical cord blood (Erices A et al., Br J Haematol., 109:235-242, 2000) and it has been proven that the cells have MAPC cell-level multipotency enabling them to differentiate into osteoblasts, adipocytes and neuron-like cells ex vivo (Lee O K et al., Blood., 103:1669-1675, 2004). Further, it was a common belief that the number of mesenchymal cells taken from umbilical cord blood at first was very small and the proliferation thereof was very difficult. But, according to recent reports, it has been proven that ex vivo amplification of the umbilical cord blood-derived mesenchymal stem cells is possible to obtain a large number of mesenchymal stem cell (Yang S E et al, Cytotherapy, 6:476-486, 2004; and Kern S H et al., Stem Cells, 24:1294-1301, 2006).

It has been reported that these cells still possess multipotency even after amplification, and can be differentiated into osteoblasts, chondroblasts, adipocytes and neuron-like cells ex vivo, while differentiating in vivo into nerve cells with the migrating ability, cartilage and bone cells, cells of hematopoietic system and liver cells (Kogler G et al., J Exp Med., 200:123-135, 2004).

Methodologically, the umbilical cord blood extracted from the real placental tissue is an ideal source for autologous and allogeneic stem cells, and such stem cells obtained thereby can be used directly or after amplifying stage whenever and as many as required.

However, there has been no attempt to apply the umbilical cord blood-derived stem cell transplantation to the developmental and/or chronic lung diseases. There are a few experimental reports that the adult bone marrow stem cells transplanted into a mouse with pneumonia induced by irradiation were differentiated into bronchial cells and type II cells of lung parenchyma (Theise N D et al. Exp Hematol., 30:1333-1338, 2002), and reduced the bleomycin-induced pulmonary fibrosis in adult animal models (Ortiz L et al. Proc Natl Acad Sci USA, 100:8407-8411, 2003; and Rojas M et al., Am J Respir Cell Mol Biol, 33:145-152, 2005).

There are some patents aimed for treatment of diseases using the umbilical cord blood-derived cells. For example, Korean Patent Publication No. 2003-0015160 describes a composition for treating articular cartilage damage comprising cell components separated, proliferated or differentiated from the umbilical cord blood and a medium containing thereof, and Korean Patent Publication No. 2005-0105467 describes a method for treating myelodysplastic syndrome and myelosclerosis by administering a high dose of umbilical cord blood-derived stem cells. However, there have been no descriptions on the therapeutic effect of the transplantation of umbilical cord blood-derived stem cells in treating developmental and/or chronic lung diseases.

Thus, the present inventors established a bronchopulmonary dysplasia model by administering highly concentrated oxygen continuously, and then administered umbilical cord blood-derived mesenchymal stem cells to the bronchopulmonary dysplasia model. As a result, pulmonary alveoli were increased in their numbers and developed normally, and the administered cells were differentiated into lung parenchymal cells. Thus, the present inventors have completed this invention by confirming that the umbilical cord blood-derived mesenchymal stem cells of the present invention can be effectively used for the treatment of lung diseases.

SUMMARY OF THE INVENTION

Accordingly, it is an object of the present invention to provide a method of treating lung diseases comprising administering cells separated or proliferated from umbilical cord blood to a patient suffering from such diseases.

It is another object of the present invention to provide a composition for treating lung diseases comprising cells separated or proliferated from umbilical cord blood as an active ingredient.

BRIEF DESCRIPTION OF THE DRAWINGS

The patent of application file contains at least one drawing executed in color. Copies of this patent or patent application publication with color drawing(s) will be provided by the Office upon request and payment of the necessary fee.

The above and other objects and features of the present invention will become apparent from the following description of the invention, when taken in conjunction with the accompanying drawings, which respectively show.

NC: normal control group,

HC: hyperoxia-exposed (bronchopulmonary dysplasia) group,

HT: hyperoxia-exposed and UCB-derived mesenchymal stem cell intratracheal transplanting group, and HP: hyperoxia-exposed and UCB-derived mesenchymal stem cell intraperitoneal transplanting group.

Figure 5:
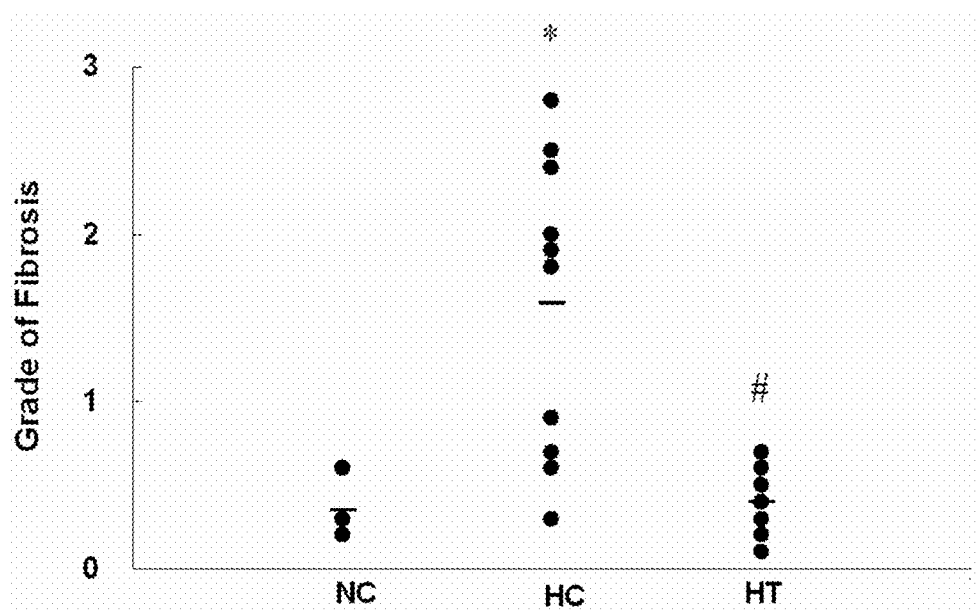

FIG. 5: a graph illustrating improved fibrosis of lung tissues of neonatal rats induced with bronchopulmonary dysplasia, one of the developmental and/or chronic lung diseases, which was determined by microscopic examination of the lung tissues after treating with UCB-derived mesenchymal stem cells according to the present invention.

Figure 1:
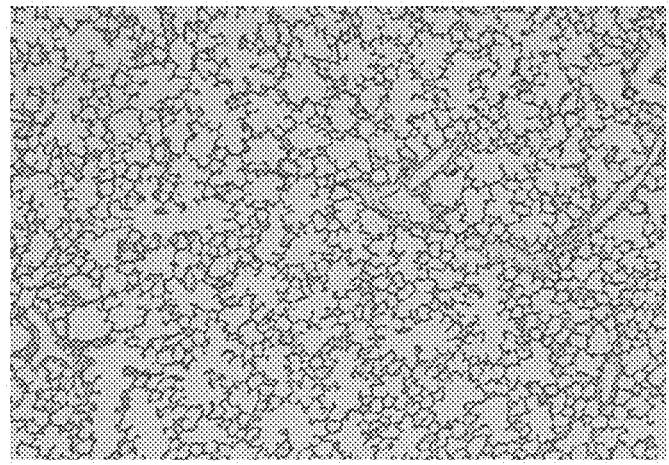
FIGS. 1 to 4: photographs illustrating the improved pathological views of the lung tissues of neonatal rats induced with bronchopulmonary dysplasia, one of the developmental and/or chronic lung diseases, after treating with umbilical cord blood (UCB)-derived mesenchymal stem cells according to the present invention.
Figure 2:
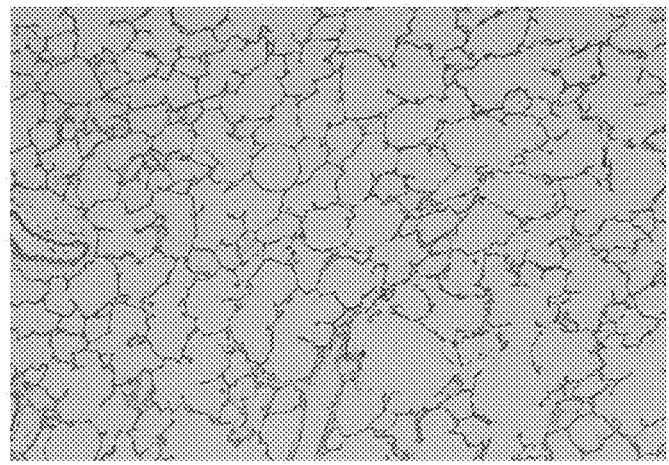
Figure 3:
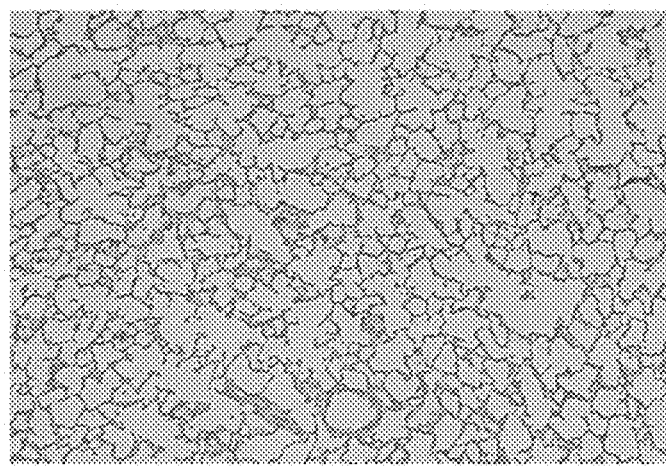
Figure 4:
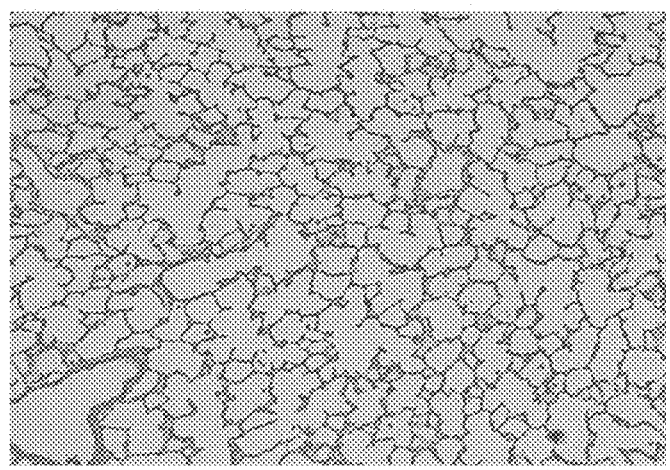

NC, HC and HT have the same meanings as defined in FIGS. 1 to 3.

*significant difference from NC group (p<0.05)
significant difference from HC group (p<0.05)

Figure 6:
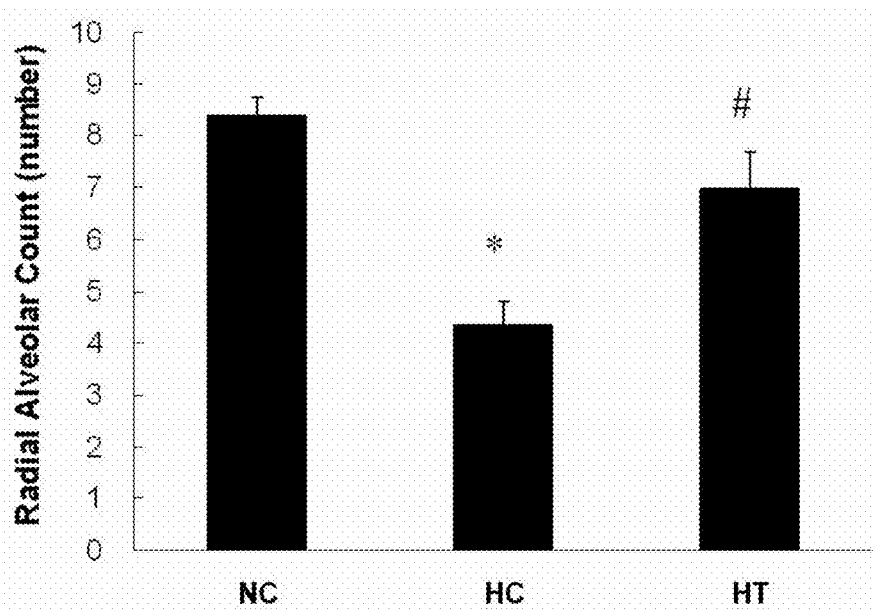
Figure 7:
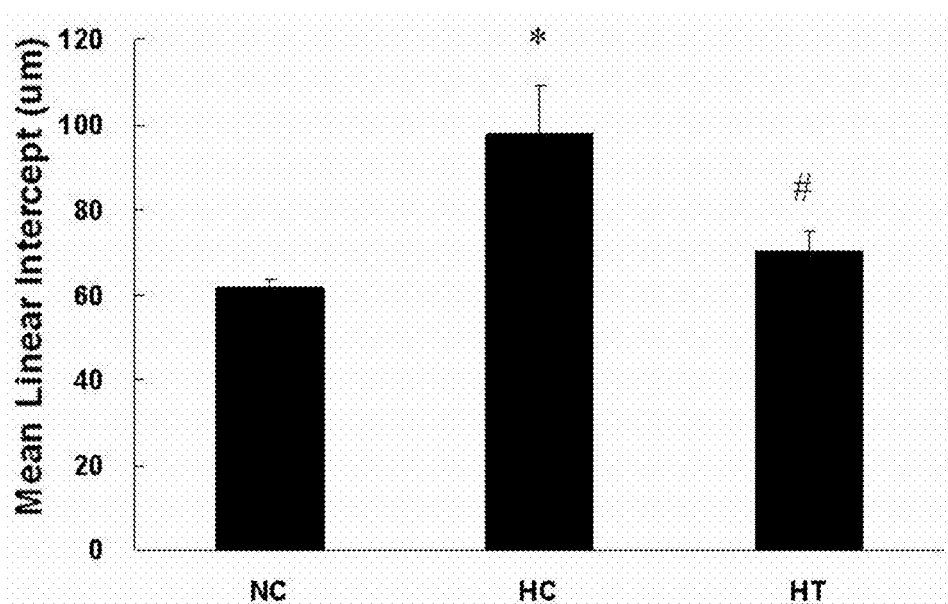
Figure 8:
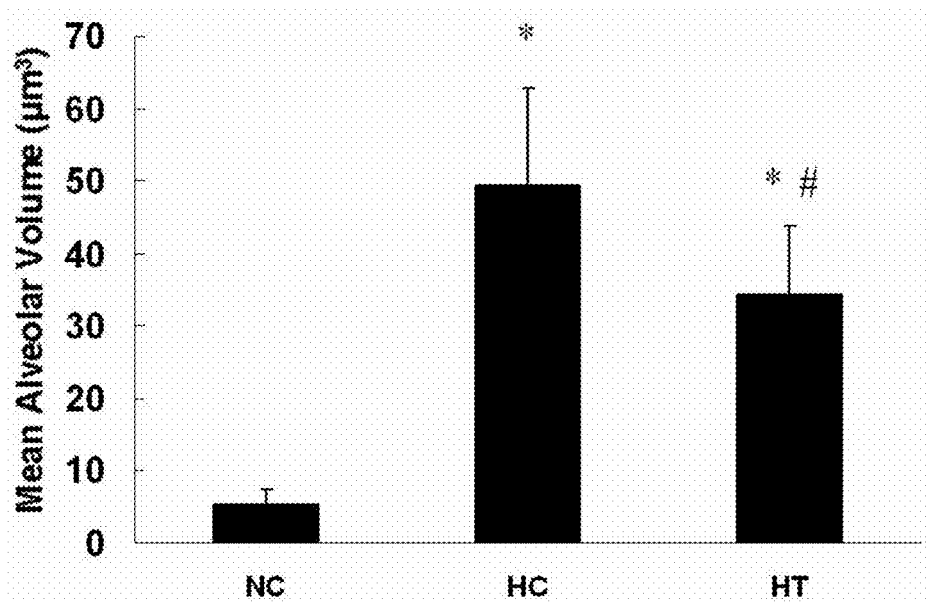

FIGS. 6 to 8: graphs illustrating the improved alveolar development in the lung tissues of neonatal rats induced with bronchopulmonary dysplasia, one of the developmental and/or chronic lung diseases, which was represented by the values of radial alveolar count (RAC), mean linear intercept (MLI) and mean alveolar volume, respectively, after treating with UCB-derived mesenchymal stem cells according to the present invention.

NC, HC, HT, * and # have the same meanings as defined in FIGS. 1 to 5.

Figure 9:
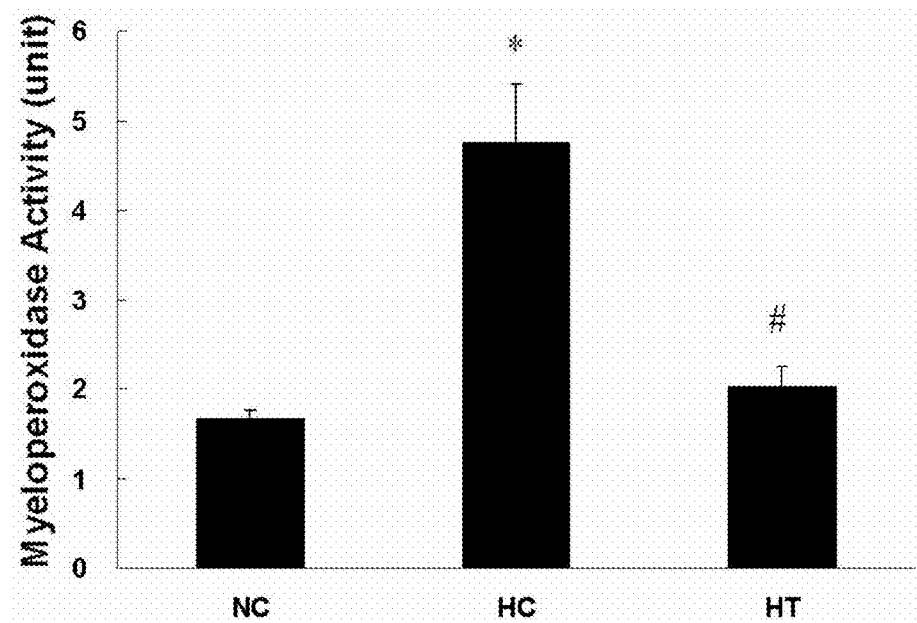

FIG. 9: a graph illustrating reduced myeloperoxidase (MPO) activity, which representing the accumulation of neutrophils as inflammatory cells, in the lung tissues of neonatal rats induced with bronchopulmonary dysplasia, one of the developmental and/or chronic lung diseases, after treating with UCB-derived mesenchymal stem cells according to the present invention.

NC, HC, HT, * and # have the same meanings as defined in FIGS. 1 to 5.

Figure 10:
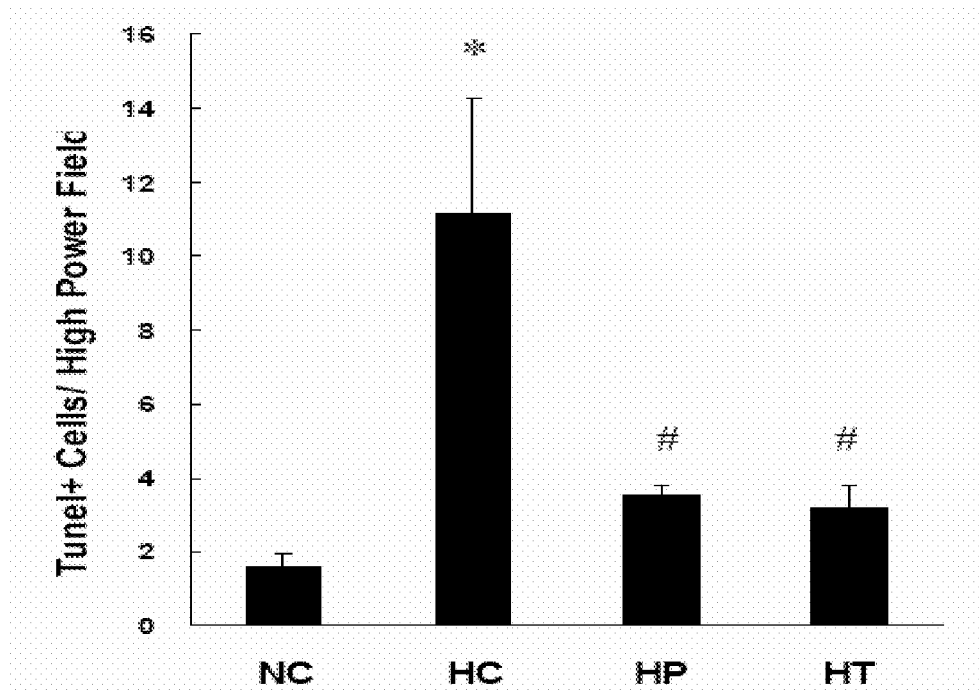

FIG. 10: a graph illustrating improved apoptosis of the lung tissue cells of neonatal rats induced with bronchopulmonary dysplasia, one of the developmental and/or chronic lung diseases, which was determined by TUNEL staining after treating with UCB-derived mesenchymal stem cells according to the present invention.

NC, HC, HP, HT, * and # have the same meanings as defined in FIGS. 1 to 5.

Figure 11:
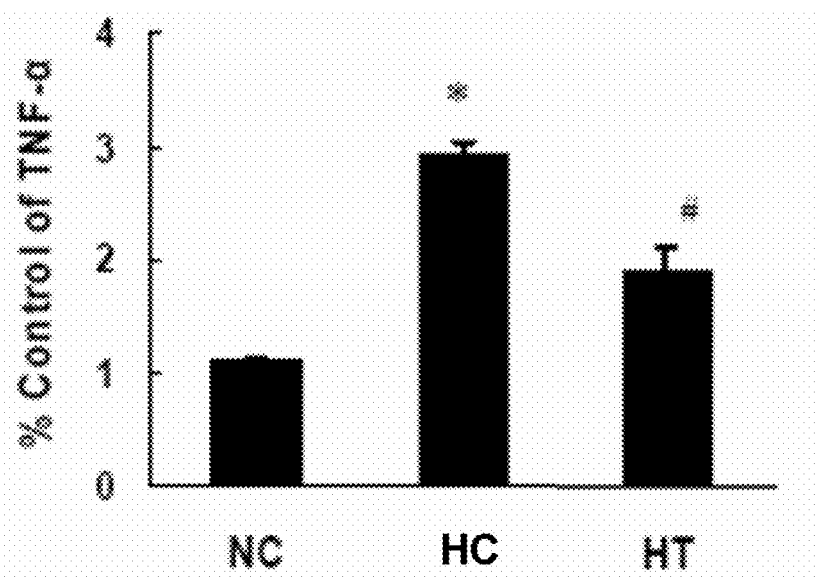
Figure 12:
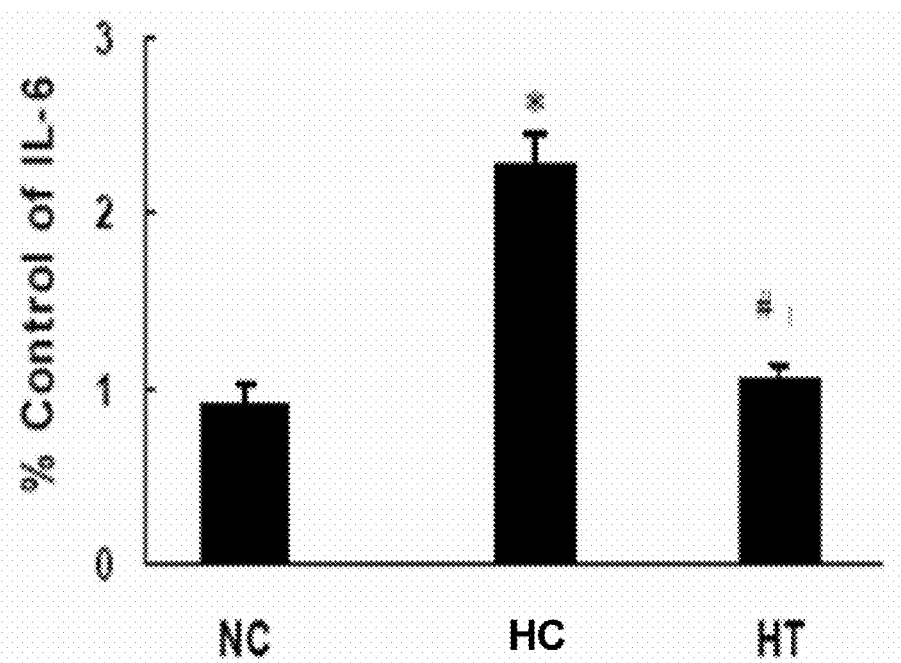
Figure 13:
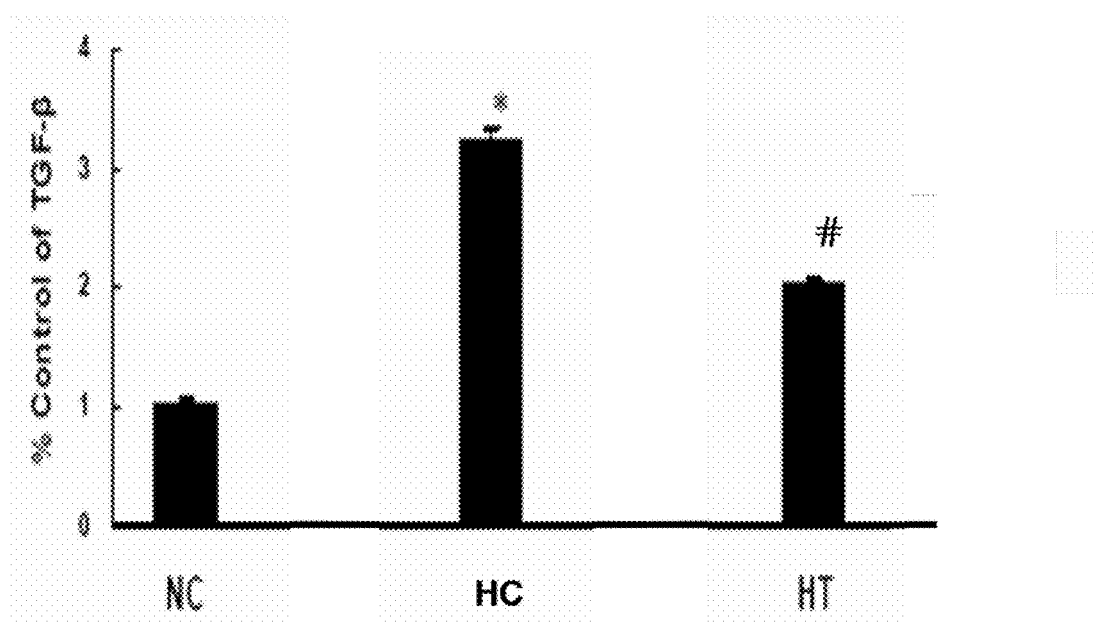

FIGS. 11 to 13: graphs illustrating improved inflammatory response and fibrotic reaction of the lung tissues of neonatal rats induced with bronchopulmonary dysplasia, one of the developmental and/or chronic lung diseases, which was represented by TNF-α, IL-6 and TGF-β values, respectively, after treating with human UCB-derived mesenchymal stem cells according to the present invention.

NC, HC, HT, * and # have the same meanings as defined in FIGS. 1 to 5.

Figure 14:
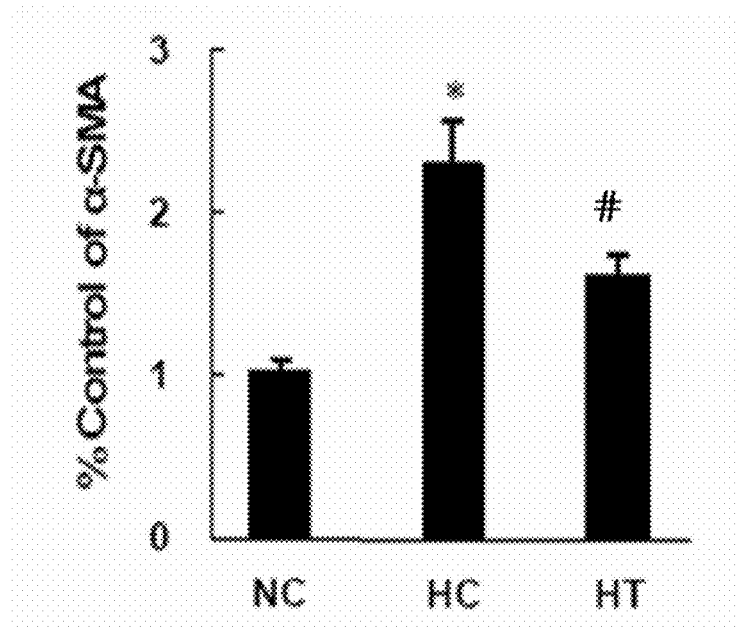
Figure 15:
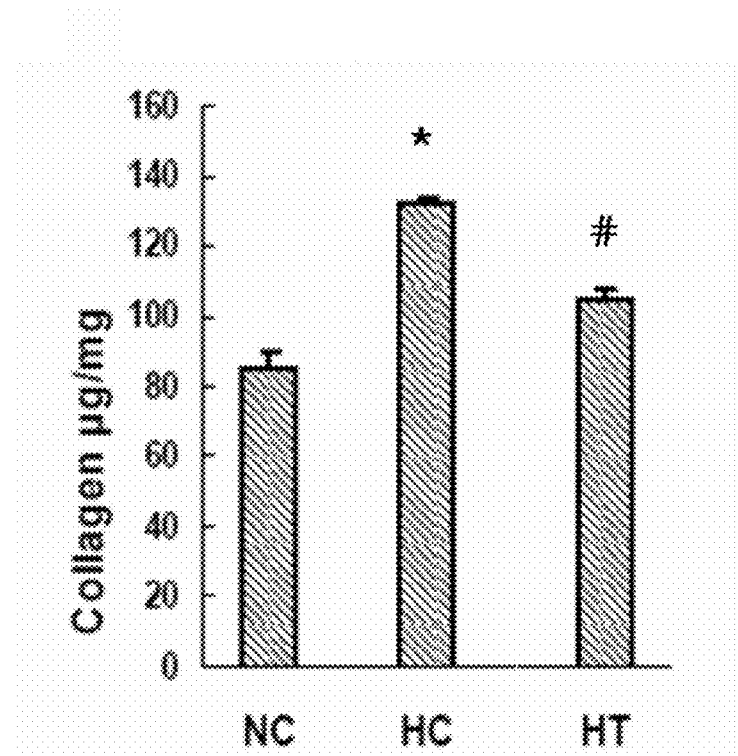

FIGS. 14 and 15: graphs illustrating improved fibrosis of the lung tissues of neonatal rats induced with bronchopulmonary dysplasia, one of the developmental and/or chronic lung diseases, which were represented by α-SMA and collagen, respectively, after treating with human UCB-derived mesenchymal stem cells according to the present invention.

NC, HC, HT, * and # have the same meanings as defined in FIGS. 1 to 5.

Figure 16:
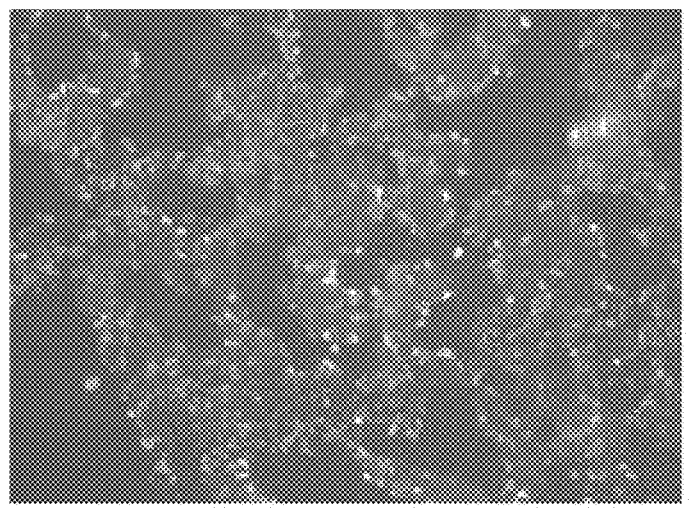

FIG. 16: a photograph illustrating that the transplanted therapeutic cellular components were safely located in the lung tissue of a neonatal rat induced with bronchopulmonary dysplasia, after treating with human UCB-derived mesenchymal stem cells according to the present invention.

Figure 17:
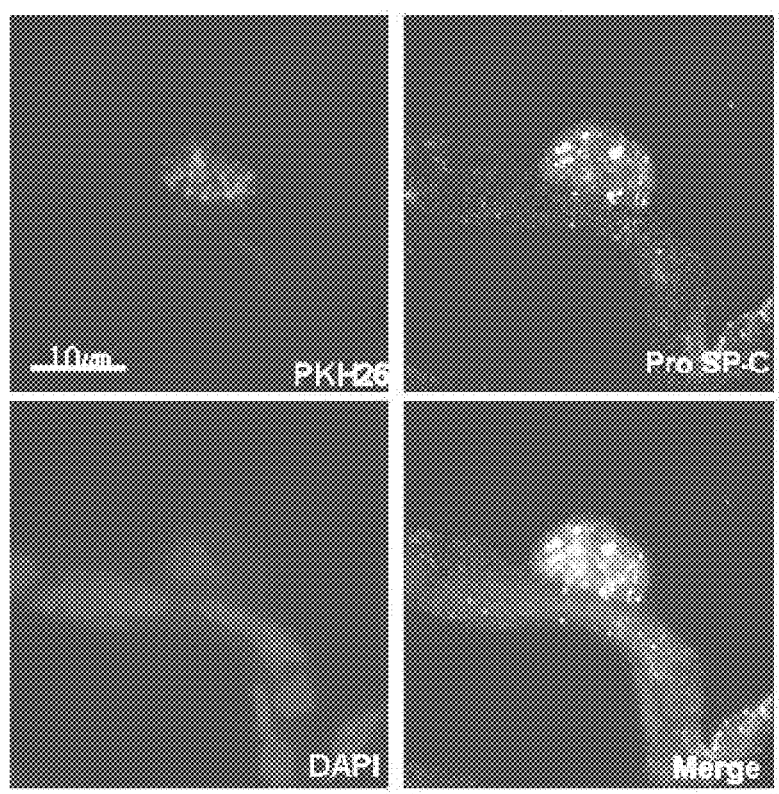

FIG. 17: a photograph illustrating that the transplanted therapeutic cellular components were safely located in the lung tissue of a neonatal rat induced with bronchopulmonary dysplasia and differentiated into type II cells of lung parenchyma, after treating with human UCB-derived mesenchymal stem cells according to the present invention; and PKH26: transplanted therapeutic cells labeled with PKH26

Pro SP-C: type II cells of lung parenchyma labeled with Pro SP-C

DAPI: cell nuclei labeled with DAPI

Merge: co-label with PKH26, Pro SP-C and DAPI

Figure 18:
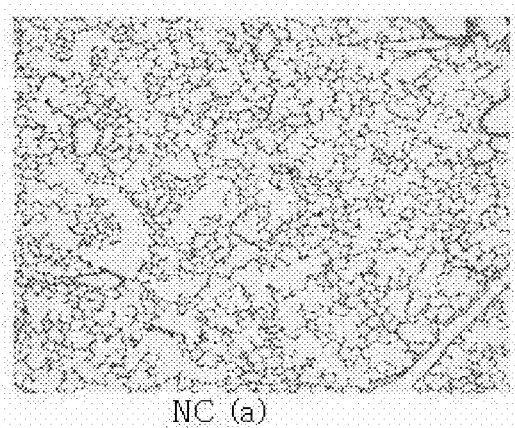
Figure 18:
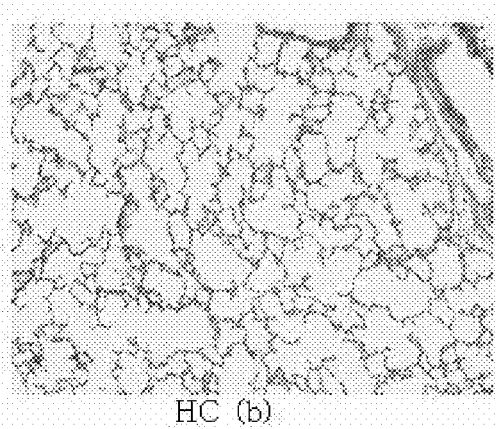
Figure 18:
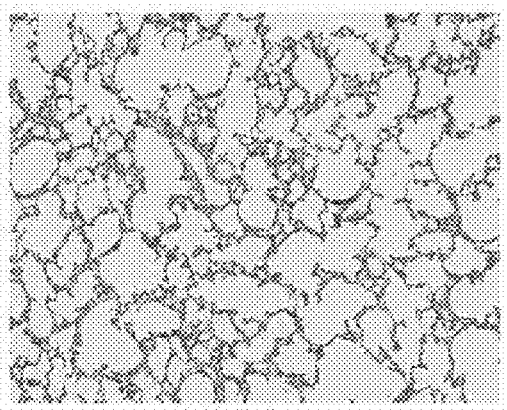
Figure 18:
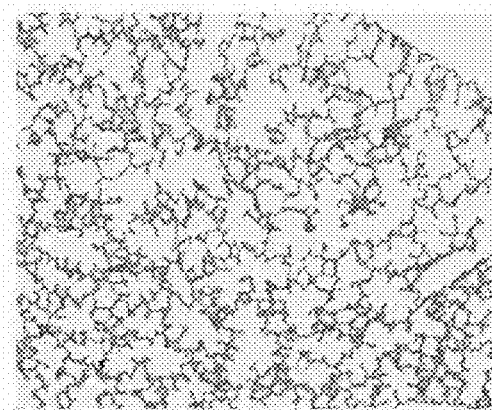

FIG. 18: a comparative photograph illustrating the pathological views of the lung tissues of neonatal rats induced with bronchopulmonary dysplasia, one of the developmental and/or chronic lung diseases, after treating with human UCB-derived mesenchymal stem cells according to the present invention and conventional human bone marrow-derived mesenchymal stem cells.

NC, HC and HT have the same meanings as defined in FIGS. 1 to 3.

BT: hyperoxia-exposed and bone marrow-derived mesenchymal stem cell intratracheal transplanting group.

DETAILED DESCRIPTION OF THE INVENTION

The present invention provides a method of treating lung diseases comprising administering cells separated or proliferated from umbilical cord blood to a patient suffering from such diseases.

Umbilical cord blood, the origin of therapeutic cells of the present invention, is the blood taken from umbilical vein connecting placenta and a fetus, and a natural by-product of childbirth. The umbilical cord blood is much easier to obtain than general mesenchymal tissues like bone marrow requiring several steps of operation, and it is also very easy to find a donor because umbilical cord blood deposit industry has been developing steadily and the related infrastructure has already been established. In addition, umbilical cord blood-originated cells do not express histocompatibility antigen HLA-DR (class II) which is the major cause of rejection after tissue—or organ transplantation (Le Blanc, K C, *Exp Hematol*, 31:890-896, 2003; and Tse W T et al., *Transplantation*, 75:389-397, 2003). Thus, these cells can minimize the immune response when transplantation is conducted, for example rejection against transplanted tissue or organ, suggesting that autologous as well as allogeneic umbilical cord blood can be used.

The procedure for the extraction and separation of umbilical cord blood is as follows.

In case of normal vaginal delivery, placenta is still in the uterus right after childbirth, and umbilical vein is expelled. Thus, umbilical cord blood is extracted from the exposed umbilical vein. In case of cesarean section, placenta is also expelled right after childbirth, and umbilical cord blood is extracted from the exposed umbilical vein.

When umbilical cord blood is taken from the exposed umbilical vein right after childbirth, the umbilical cord blood is extracted from the umbilical vein connecting the placenta and the fetus by aseptic manipulation. At this time, umbilical cord blood can be taken either before or after placental separation from uterus. In the case of cesarean section, the umbilical cord blood is extracted from the umbilical vein ex vivo after placental separation from uterus, and taken into an umbilical cord blood sampling bag containing anticoagulant using a sampling needle.

The inventive cells separated or proliferated from the umbilical cord blood may be one or more cells selected from the group consisting of monocytes containing hematopoietic stem cells and mesenchymal stem cells separated from the umbilical cord blood, mesenchymal stem cells separated from the umbilical cord blood, and mesenchymal stem cells amplified from the mesenchymal stem cells by sub-culture. The mesenchymal stem cells separated from the umbilical cord blood or the mesenchymal stem cells amplified from the mesenchymal stem cells by sub-culture are more preferred.

The mesenchymal stem cells separated from the umbilical cord blood are multipotent, unlike the typical stromal cells of bone marrow, suggesting that they can be differentiated into mesenchymal tissues such as bone, cartilage, adipose tissue, muscle, tendon, etc., under appropriate conditions. Further, umbilical cord blood-derived mesenchymal stem cells have self-renewal ability, suggesting that they are capable of proliferating under suitable conditions without differentiating into specific cells or tissues, and might exhibit anti-inflammation activity when transplanted. In addition, the cells are more primitive and have much better cell proliferation, differentiation and secretory capacity of the regulatory molecules or substances, as compared with those derived from the mesenchymal stem cells separated from general mesenchymal tissues such as bone marrow, muscle and skin.

To separate and culture the mesenchymal stem cells from the harvested umbilical cord blood, any of the methods described in Korean Patent Publication No. 2003-0069115 and published articles including (Pittinger M F et al. *Sci-* ence, 284:143-7, 1999; and Lazarus H M et al. *Bone Marrow Transplant,* 16:557-64, 1995) can be used, and one example is shown below.

First, the harvested umbilical cord blood is for example, centrifuged by using Ficoll-Hypaque gradient to separate monocytes comprising hematopoietic stem cells and mesenchymal stem cells, which are then washed several times to eliminate impurities. The washed monocytes are cultured in a culture vessel with proper density, and then, the cells are allowed to proliferate to form a single layer. Among the proliferating cells, those who are observed to be homogeneous and to form a colony of a spindle shape under phase contrast microscopy, are the mesenchymal stem cells. When the cells are proliferated, sub-cultures are performed until the cells are amplified enough.

The inventive umbilical cord blood-derived cells can be cryopreserved in accordance with the conventional method well-known to those in the art (Doyle et al., 1995). That is, the cells may be suspended at the concentration of $1 \times 10^6 \sim 5 \times 10^6$ cells per 1 Ml in a medium for the cryopreservation comprising 10% to 20% FBS (fetal bovine serum) and 10% DMSO (dimethylsulfoxide).

The cell suspension may be distributed into glass- or plastic ampoules for deep freezing, and then the ampoules may be sealed and put in a deep freezer kept at a programmed temperature. At this time, it is preferred to use a freeze-program that controls the freezing rate at $-1°$ C./min so that cell damage during thawing can be minimized. When the temperature of the ampoule reaches $-90°$ C., it is transferred into a liquid nitrogen tank and maintained at less than $-150°$ C.

To thaw the cells, the ampoule has to be transferred from the liquid nitrogen tank into a 37° C. water bath quickly. The thawed cells in the ampoule are placed in a culture vessel containing a culture medium quickly under an aseptic condition.

In the present invention, the medium used in the separation or proliferation of the mesenchymal stem cells may be any medium for general cell culture well-known to those in the art containing 10% to 30% FBS, for example, Dulbecco's modified eagle medium (DMEM), minimum essential medium (MEM), α-MEM, McCoys 5A medium, Eagle's basal medium, CMRL (Connaught Medical Research Laboratory) medium, Glasgow minimum essential medium, Ham's F-12 medium, IMDM (Iscove's modified Dulbecco's medium), Liebovitz' L-15 medium, RPMI (Roswell Park Memorial Institute) 1640 medium, and DMEM is preferred. The cells may be suspended at the concentration of $5 \times 10^3 \sim 2 \times 10^4$ cells per 1 Ml of the medium.

Further, the cell culture medium of the present invention can additionally include one or more auxiliary components, for example, fetal bovine serum, horse serum or human serum; and antibiotics such as Penicillin G, streptomycin or gentamycin sulfate, antifungal agent such as amphotericin B or nystatin, and a mixture thereof to prevent microorganism contamination.

According to some embodiments of the inventive method, umbilical cord blood-derived cells may be intratracheally administered as close to the lung tissue, thereby increasing therapeutic effect by elevating accessibility.

The lung diseases may be developmental and/or chronic lung diseases selected from cystic fibrosis, chronic obstructive pulmonary disease and bronchopulmonary dysplasia.

In some embodiments of the present invention, the obtained umbilical cord blood was centrifuged to separate monocytes, and then the separated cells were cultured with an appropriate density in a culture vessel. When the cells were grown to an appropriate density, sub-cultures were performed. Further, a bronchopulmonary dysplasia model in neonatal rats was established by administering highly concentrated oxygen continuously from the birth. As a result, rats with bronchopulmonary dysplasia thus obtained exhibited increased respiratory rate and poor weight gain. Then, the lungs were extracted from the rat and stained. As a result, rats with bronchopulmonary dysplasia (HC) exhibited chronic inflammatory responses with increased monocytes and fibrosis with over-proliferated interstitial fibroblasts in the lung (see FIGS. 2, 5, 10 to 15). In addition, in the lung tissue of the rat (HC), radial alveolar count (RAC, see Husain A N et al., *Pediatr Pathol.,* 13:475-484, 1993) representing the number of alveoli was significantly lowered, mean linear intercept (MLI, see Dunnill M S., Thorax 17:320-328, 1962) representing the size of alveoli and mean alveolar volume (see McGowan S et al., *Am J Respir Cell Mol Biol.,* 23:162-167,2000) increased remarkably (see FIGS. 6 to 8), and resultantly alveolar development was significantly abnormal, compared with that in the wild type normal rat (NC). However, in the lung tissues of the rats administered with the umbilical cord blood-derived mesenchymal stem cells (HP, HT), the damage was moderated (see FIGS. 3 to 5, 10 to 15), RAC increased, and MLI and mean alveolar volume became lower (see FIGS. 6 to 8).

Further, the result of measurement of myeloperoxidase (MPO) activity as the index of neutrophil accumulation shows that MPO activity in the lung tissues of hyperoxia-exposed neonatal rat (HC) increased markedly as compared with that of room air-exposed rat, while MPO activity in the lung tissues of rats administered with the umbilical cord blood-derived mesenchymal stem cells (HT) was markedly lower than that of the hyperoxia-exposed neonatal rats (see FIG. 9), which means that lung damage mediated by the accumulation of neutrophils as inflammatory cells was significantly reduced.

In addition, umbilical cord blood-derived mesenchymal stem cells labeled with red fluorescent PKH26 was intratracheally administered to rats and then the lung tissues of the rats were observed with a fluorescent microscope. As a result, the umbilical cord blood-derived mesenchymal stem cells were safely located in the lungs (see FIG. 16), and the parts of the cells safely located in the lung tissues were differentiated into lung parenchymal cells (see FIG. 17).

Accordingly, the cells of the present invention, which are separated and proliferated from umbilical cord blood, can be effectively used to treat lung diseases such as developmental and/or chronic lung diseases comprising adult chronic obstructive lung diseases (COPD) (e.g., cystic fibrosis and emphysema) and bronchopulmonary dysplasia of a infant and a premature baby.

The present invention also provides a composition for treating lung diseases comprising the above-described cells separated or proliferated from umbilical cord blood as an active ingredient.

The inventive composition can additionally comprise one or more auxiliary components selected from the group consisting of a medium to suspend the cells, a gene effective in the treatment of lung disease (e.g., anti-inflammatory cytokine gene, siRNA or anti-sense primer against inflammatory cytokine) or an expression vector comprising thereof, a cytokine providing autocrine or paracrine effect (e.g., interleukin-10), growth factor (e.g., karatinocyte growth factor), and a mixture thereof.

At this time, the medium may be identical with those described above for the cell culture medium, except for not including any serum, antibiotics and antifungal agent.

The gene or the expression vector comprising thereof may be transferred by any of the conventional methods known to those in the art, for example, viral transfection or non-viral method, or simply combined with the cells. At this time, the introduction of the gene may be conducted in accordance with any of the methods known to those in the art including adenoviral transformation, gene gun, liposome-mediated transformation, and retrovirus or lentivirus-mediated transformation, plasmid or adeno-associated virus without limitation. Further, the cells may be transplanted together with carriers having gene delivery system, which can release or deliver a gene to the cells for long periods of time.

Further, the composition of the present invention may include $1.0 \times 10^5$ to $1.0 \times 10^9$ cells/Mℓ, preferably $1.0 \times 10^6$ to $1.0 \times 10^8$ cells/Mℓ, more preferably $1.0 \times 10^7$ cells/Mℓ.

The inventive composition can be used as not-frozen or can be frozen for later use. To freeze the composition, a standard cryopreservative agent (e.g., DMSO, glycerol, Epilife™ or cell freezing medium (Cascade Biologics)) may be added to the cells.

Further, the composition can be administered by formulating a unit dosage suitable for administering to a patient by conventional methods in the pharmaceutical field, and the dosage contains an effective amount enough to induce alveolar development by a single dose or in divided doses. For this purpose, a formulation for parenteral administration include injection formulation such as injection ampoule, infusion formulation such as infusion bag, and spray formulation such as aerosol preferably. The injection ampoule may be mixed with injection solution such as saline solution, glucose, mannitol and ringer's solution just before use. Further, the cells can be carried by infusion bag textured by polyvinyl chloride or polyethylene, for example, a product of Baxter, Becton-Dickinson, Medcep, National Hospital Products or Terumo.

The pharmaceutical formulation of the present invention may additionally comprise one or more pharmaceutically acceptable inactive carriers except for the active ingredient, for example, preservative, analgesic controller, solubilizer or stabilizer for injection formulation, and base, excipient, lubricant or preservative for topical formulation.

The prepared composition or pharmaceutical formulation of the present invention can be administered in accordance with any conventional method in the art together with other stem cells used for transplantation and other purposes, or in the form of a mixture therewith. Direct engraftment or transplantation to the lesion of the lung, or transplantation or injection into airway is preferred, but not always limited thereto. Further, both non-surgical administration using catheter and surgical administration such as injection or transplantation after thoracotomy are possible, but non-surgical administration using catheter is more preferred. In addition, the composition or therapeutic agent can also be administered parenterally, for example, intravenous injection, one of the conventional methods for transplantation of stem cells of hematopoietic system, besides direct administration to the lesion.

The cells separated or proliferated from umbilical cord blood of the present invention can be administered in an effective amount ranging from about $1.0 \times 10^4$ to $10.0 \times 10^{10}$ cells/kg (body weight), preferably $1.0 \times 10^5$ to $1.0 \times 10^9$ cells/kg (body weight) per day in a single dose or in divided doses. However, it should be understood that the amount of the active ingredient actually administered ought to be determined in light of various relevant factors including the disease to be treated, the condition to be treated, the severity of the patient's symptom, the chosen route of administration, and the body weight, age and sex of the individual patient; and, therefore, the above dose should not be intended to limit the scope of the invention in any way.

As described above, umbilical cord blood is a natural by-product of childbirth. The umbilical cord blood is much easier to obtain than general mesenchymal tissue-like bone marrow requiring several steps of operation and it is also very easy to find a donor because umbilical cord blood deposit industry is developing steadily and the related infrastructure has already been established. In addition, umbilical cord blood-originated cells do not express histocompatibility antigen HLA-DR (class II) which is the major cause of rejection after tissue- or organ transplantation. Thus, these cells can minimize the immune response when transplantation is conducted, for example rejection against transplanted tissue or organ, suggesting that autologous as well as allogeneic umbilical cord blood can be used. From the above advantages, the inventive method can effectively treat lung diseases, especially developmental and/or chronic lung diseases comprising cystic fibrosis, chronic obstructive pulmonary disease and broncopulmonary dysplasia.

The following Examples are intended to further illustrate the present invention without limiting its scope.

EXAMPLE 1

Separation and Culture of Cells

The therapeutic cells of the present invention, mesenchymal stem cells, were separated from human umbilical cord blood and cultured as follows (see Yang S E et al., Cytotherapy, 6(5):476-86, 2004).

<1-1> Extraction of Umbilical Cord Blood (UCB)

UCB sample was collected from the umbilical vein right after childbirth with the mother's approval. Specifically, the umbilical vein was pricked with a 16G needle connected to an UCB-collection bag containing 23 or 44.8 Mℓ of a CDPA-1 anticoagulant (Green cross corp., Korea) such that the UCB was collected into the collection bag by gravity. The UCB thus obtained was handled within 48 hours after collection, and the viability of the monocytes was more than 90%.

<1-2> Separation and Amplification of Mesenchymal Stem Cells

The UCB collected in <1-1> was centrifuged by using Ficoll-Hypaque gradient (density: 1.077 g/cm$^3$, Sigma, USA) to obtain monocytes. The resulting cells were washed with a basal medium ($\alpha$-MEM medium (Gibco BRL, USA) supplemented with 10% to 20% FBS (HyClone, USA)) several times. $5 \times 10^6$ cells/cm$^2$ were inoculated into a basal medium, suspended, and incubated at 37° C. under a humid condition containing 5% CO$_2$, while replacing the medium with a fresh medium twice a week. As a result, adherent fibroblast-like cells were identified.

Within 3 weeks, 0.25% Trypsin (HyClone) was added to a monolayer colony of the mesenchymal stem cells, and the cells were washed. Then, $5 \times 10^4$ cells/cm$^2$ were inoculated into a basal medium and repeated subcultivation was conducted so that the cells expanded ex vivo.

EXAMPLE 2

Hyperoxia-exposed Bronchopulmonary Dysplasia Model

All animal tests were approved by Research Animal Laboratory Committee of Samsung Biomedical Research Institute (Korea), and conducted in accordance within their guideline.

First, in order to establish a bronchopulmonary dysplasia model, timed-pregnant Sprague-Dawley rats (Daehan biolink Co. Ltd.) were purchased and raised in a research animal cage for at least 1 week before childbirth. Highly concentrated oxygen was administered into the neonatal rats right after their birth (within 10 hours from the birth) for 14 days.

Specifically, the rat dams and the neonates were put in a 69.5×50.0×32.0 cm acryl box (sealed Plexiglas cage) which was controlled as at a humidity 40-60% and a temperature 23-26° C. under 1 atm, then the box was saturated with 100% oxygen at a rate of 10 l/min for the first 10 minutes. When the oxygen saturation reached 95%, measured by an oxygen analyzer (572, Servomex, USA), 100% oxygen was refluxed at a rate of 2.5 l/min, during which the oxygen saturation was measured continuously to keep the oxygen saturation at around 95%. To avoid pulmonary edema caused by oxygen toxicity, nursing rat dams were switched between room air and 95% $O_2$ every 24 hour for 14 days.

EXAMPLE 3

Administration of UCB-derived Mesenchymal Stem Cells 0.05 Ml of UCB-derived 5.83×10$^5$ mesenchymal stem cell suspension in α-MEM without FBS was intraperitoneally or intratracheally administered to the neonatal rats of Example 2. The intratracheal administration was performed using a 26-gauge needle on the 5$^{th}$ day from birth after confirming pup-up of air from tracheae in the midline areas of the necks of the rats.

EXAMPLE 4

Tissue Preparation After Animal Sacrifice

On the 14$^{th}$ day, the rats were anesthetized by intraperitoneal pentobarbital injection. After fixing the limbs, thoracotomy was performed to expose their hearts and lungs. A part of the sacrificed rats was subjected to transcardiac perfusion with ice cold PBS to extract the hearts and the lungs. A catheter was inserted intratracheally and fixed tightly. 4% formaldehyde as a fixative was instilled through the inserted catheter, and the lungs were expanded uniformly under the pressure of 25 cm $H_2O$ followed by fixing with the fixative. Further, the lungs of the other rats were extracted and immediately frozen in liquid nitrogen.

EXAMPLE 5

Measurement of Grade of Fibrosis, RAC, MLI and Mean Alveolar Volume

The lung tissue sections fixed with 4% formaldehyde for 24 hours in Example 4 were embedded in paraffin, which were then cut into 4 μm thick slices which were stained with hematoxylin eosin, followed by observation under optical microscope, to determine the number of neutrophils, the grade of fibrosis, the cell numbers and thickness of alveolar septa and pulmonary interstitium, while the presence or absence of pulmonary edema was investigated. Radial alveolar count (RAC) representing the newly-formed saccules and alveoli and mean linear intercept (MLI) representing the size of alveoli were measured, and mean alveolar volume was calculated.

The grade of fibrosis was assessed quantitatively according to a modification of the method described in (Stocker, J. T, Hum Pathol., 17:943-961, 1986). Specifically, 6 non-overlapped lung tissue sections per rat were randomly selected, and 5 fields per section, totally to 30 fields, were observed at a magnification of ×10. The grade of fibrosis was scored as follows: Grade 0=normal lung; Grade 1=minimal fibrosis of alveolar septa; Grade 2=moderate fibrosis of alveolar septa; and Grade 3=severe fibrosis of alveolar septa. The fibrosis score was expressed as a mean grade of fibrosis for each sample.

To measure RAC (see Husain A N et al., *Pediatr Pathol.*, 13:475-484, 1993), a vertical line was drawn from the terminal bronchiole to the nearest fibrovascular septum, and the number of saccules between the terminal bronchiole and the fibrovascular septum was counted.

MLI (see Dunnill M S., *Thorax* 17:320-328, 1962) was calculated using 1 mm ruler, counting the number of septum while observing the tissue under the optical microscope (×40).

To measure RAC and MLI, randomly selected areas were each observed at the 10 fields.

For the calculation of mean alveolar volume (see McGowan S et al., *Am J Respir Cell Mol Biol.*, 23:162-167, 2000), a grid that contained equally spaced crosses was placed on the photomicrograph of the distal lung magnified 200 times, and the diameters of the alveoli that were within each of the cross were measured. The cube of the alveolar diameter times π and divided by 3 was used to estimate the mean alveolar volume, and the resulting values obtained from 6 photos randomly selected for a test rat were averaged.

Each data was analyzed statistically by using corresponding mean value. The image of each section was taken by a digital camera of Olympus BX81 microscope. Data are expressed as mean±SD, and statistical analysis was performed by analysis of variance (ANOVA), followed by the Mann-Whitney test or Kruskal-Wallis test using an SAS (enterprise guide version of three, SAS Institute, USA) (Results were considered significant when the p value was less than 0.05).

As a result, the lung tissue of a bronchopulmonary dysplasia-induced rat (HC) showed chronic inflammatory responses accompanied by increased number of monocytes such as alveolar macrophages and lymphocytes, and fibrosis accompanied by over-proliferation of interstitial fibroblasts. However, the damage in pathology was remarkably alleviated in the lung tissues of the rats intratracheally or intraperitoneally administered with the mesenchymal stem cells (HT) (HP) (FIGS. 1 to 4), the quantitative analysis of grade of fibrosis was markedly reduced (FIG. 5).

Further, in the lung tissue of a bronchopulmonary dysplasia-induced rat (HC), as compared with that of a normal rat (NC), RAC was significantly decreased, and MLI as well as mean alveolar volume were remarkably increased. As a result, impediment of alveolar development showing a reduced alveolar number and an abnormally enlarged alveolar size was obvious. However, in the lung tissue of the rat intratracheally administered with the mesenchymal stem cells (HT), as compared with that of the bronchopulmonary dysplasia-induced rat (HC), RAC was increased, while MLI and mean alveolar volume became lower (FIGS. 6 to 8). The result suggests that the alveolar development has been improved by showing the increased alveolar number and the decreased alveolar size.

EXAMPLE 6

MPO (Myeloperoxidase) Activity

Myeloperoxidase (MPO) activity, an index of neutrophil accumulation, was determined using a modification of the method described in (Gray K D et al., *Am J Surg.*, 186:526-530, 2003).

Specifically, the frozen lung tissue samples prepared in Example 4 were homogenized in a phosphate buffer (pH 7.4), centrifuged at 30,000×g for 30 min, and the resulting pellets were resuspended in a phosphate buffer (50 mM, pH 6.0) containing 0.5% hexadecyltrimethyl ammonium bromide. The resuspended pellets were allowed to react with 0.167 mg/Ml O-dianisidine hydrochloride and 0.0005% hydrogen peroxide, and the rate of change in the absorbance was measured at 460 nm to determine its MPO activity. 1 unit of MPO activity was defined as the quantity of enzyme degrading 1 μmol/min of peroxide. All data was expressed in mean±SD, and statistical analyses were conducted in accordance with the method of Example 5 (Results were considered significant when the p value was less than 0.05).

As a result, the MPO activity in lung tissues of hyperoxia-exposed neonatal rat (HC) was higher than that of room air-exposed rat, which means that the accumulation of neutrophils as inflammatory cells has increased significantly. However, when the mesenchymal stem cells were intratracheally administered to rats (HT), the MPO activity was significantly reduced than that of hyperoxia-exposed neonatal rats (FIG. 9), which means that the accumulation of neutrophils as inflammatory cells was significantly reduced.

EXAMPLE 7

TUNEL Staining

Apoptotic cell death in the lung tissues was determined using the immunofluorescent terminal deoxynucleotidyl transferase-mediated deoxyuridine triphosphate nick end labeling (TUNEL) technique (kit S7110 ApopTag, Chemicon, USA).

Specifically, slides with the lung paraffin sections prepared in Example 5 were mounted with a vector shield mounting solution containing DAPI (H-1200, Vector, USA) and visualized by fluorescent microscopy (Nikon E600, Nikon, Japan) at a magnification of ×20. The number of TUNEL positive cells was determined in 10 non-overlapping random fields per rat.

As a result, the number of TUNEL positive cells was significantly attenuated in the rats intraperitoneally or intratracheally administered with UCB-derived mesenchymal stem cells (HP, HT) (FIG. 10), which means that the degree of apoptotic cell death in the lung tissues was significantly reduced.

EXAMPLE 8

Measurement of the Levels of TNF-α, IL-6 and TGF-β

The mRNA levels of inflammatory cytokines, TNF-α and IL-6, and a fibrogenic cytokine, TGF-β were analyzed by semiquantitative reverse-transcriptase polymerase chain reaction (RT-PCR) to determine the degrees of lung inflammation and fibrosis.

Specifically, the total RNA in the lung tissues prepared in Example 4 was extracted using a RNA Trizol kit (Invitrogen, USA). The cDNA was synthesized from 1 μg of RNA using a ProtoScript II RT-PCR kit (New England Biolabs, USA).

Then, PCR was performed using the cDNA as a template and primers for TNF-α, IL-6, TGF-β, and glyceraldehyde-3-phosphate dehydrogenase (GAPDH). The primers were designed with Primer3 (Whitehead Institute, USA) and synthesized from Bioneer Inc. (Korea). The sequences of the primers were presented in Table 1 below.

TABLE 1

| Primers | | SEQ ID NO: |
|---|---|---|
| TNF-α | Sense | TACTGAACTTCGGGGTGATCGGTCC (SEQ ID NO: 1) |
| | Antisense | CAGCCTTGTCCCTTGAAGAGAACC (SEQ ID NO: 2) |
| TGF-β | Sense | CAACTGTGGAGCAACACGTAGA (SEQ ID NO: 3) |
| | Antisense | CAACCCAGGTCCTTCCTAAAGT (SEQ ID NO: 4) |
| IL-6 | Sense | CACCAGGAACGAAAGTCAACTC (SEQ ID NO: 5) |
| | Antisense | GGAAGCATCCATCATTTCTTTG (SEQ ID NO: 6) |
| GAPDH | Sense | CTCTACCCACGGCAAGTTCAA (SEQ ID NO: 7) |
| | Antisense | GGGATGACCTTGCCCACAGC (SEQ ID NO: 8) |

In detail, 1 μℓ of cDNA was added to a mixture of a PCR master mix (19 μℓ, Bioneer, Korea) and 0.5 uM of each primer. PCR was repeated for 33 cycles using a T1 thermocycler (Biometra, Germany) under the following conditions: denaturation at 95° C. for 60 seconds; annealing at 60° C., 58° C., 57° C. and 56° C. for 60 seconds; and extension at 72° C. for 60 seconds. The PCR products were separated by 1.2% agarose gel electrophoresis, visualized by ethidium bromide and scanned using a Gel Doc 2000 analyzer (Bio-Rad, USA). The expression level of each gene was semi-quantified by densitometric analysis using Quantity One software (Bio-Rad, USA). The relative expression level of each cytokine was determined by the density ratio of each cytokine to GAPDH (control).

As a result, the mRNA levels of TNF-α, IL-6 and TGF-β were significantly attenuated in the rats intratracheally (HT) administered with the UCB-derived mesenchymal stem cells (FIGS. 11 to 13). The result suggests that the degree of lung inflammation and fibrosis has been improved by administration of the inventive UCB-derived mesenchymal stem cells.

EXAMPLE 9

Measurement of the Levels of α-Smooth Muscle Actin (SMA) and Collagen

In order to determine the degree of lung fibrosis, α-SMA and collagen levels in the lung tissue samples were measured as follows.

First, to measure the level of α-SMA, the frozen lung tissue samples prepared in Example 4 were homogenized in a cold buffer (50 mM Tris-HCl (pH 7.4), EDTA (1 mM), EGTA (1 mM), PMSF (1 mM), KCl (42 mM) and $MgCl_2$ (5 mM)) and centrifuged at 7,000 rpm, 4° C. for 20 minutes to remove the cell debris. The protein content in the supernatant was determined by Bradford assay (Sigma-Aldrich, USA). Western blot analysis was performed using the protein and visualized by ECL kit (Amersham, USA). At this time, monoclonal anti-α-SMA antibody (1:500, Sigma-Aldrich, USA), anti-α-tubulin antibody (1:1000, Calbiochem, Germany) and anti-mouse IgG horseradish peroxidase (HRP) antibody (1:1000, Dako, USA) were used. The α-SMA expression level was determined by the density ratio of α-SMA to α-tubulin. Densitometry was performed using Image J (NIH, USA).

The collagen level of the lung tissues was determined from a total soluble collagen using a Sirocol collagen kit (Biocolor Ltd., UK).

Specifically, the frozen lung tissue samples prepared in Example 4 were homogenized in 1 ml of a 0.5 M acetic acid solution containing 1 mg pepsin (Sigma, USA) per 10 mg tissue, incubated at 4° C. for 24 hours with constant shaking and centrifuged. After the samples were centrifuged at 4° C., 10,000 rpm for 10 minutes, supernatants were stored for further analysis.

Then, 1 ml of Sircol dye reagent specifically binding to collagen was added to 100 µl of each of the resulting supernatants followed by mixing for 30 minutes and centrifugation at 4° C., 12,000 rpm for 10 minutes. The resulting pellets were suspended in 1 ml of an alkali reagent (0.5 M NaOH).

The optical density (OD) values of the test samples were evaluated at a wavelength of 540 nm by using spectrophotometry (SPECTRAFLUOR PLUS Tecan. Switzerland) and compared with those obtained with the standard collagen solution provided by the manufacturer.

As a result, the α-SMA levels and the collagen levels were significantly attenuated in the rats intratracheally (HT) administered with the UCB-derived mesenchymal stem cells (FIGS. 14 and 15). These results suggest that the degree of lung fibrosis has been improved by administration of the inventive UCB-derived mesenchymal stem cells.

EXAMPLE 10

Double-labeled Immunohistochemistry Staining

The differentiation of the mesenchymal stem cells transplanted into the lung was observed with a microscope.

First, in order to check whether the mesenchymal stem cells were properly transplanted into the lung, the mesenchymal stem cells of Example 1, labeled with red fluorescent PKH26 (Sigma, USA), were intratracheally administered to each rat with bronchopulmonary dysplasia, and then, the lung tissue of the rat was observed with a fluorescent microscope.

The result showed that the mesenchymal stem cells of Example 1 were safely located in the lung (FIG. 16).

Further, in order to check the character of differentiation of the cells located in the lung, whether the transplanted cells labeled with PKH26 were stained with pro SP-C (pro surfactant protein C) as a specific marker of type II pneumonocyte, one of cells of lung parenchyma, was examined by subjecting a frozen tissue section to immunohistochemistry staining against the cell specific marker.

Specifically, a frozen lung section was fixed with 4% paraformaldehyde for 30 min, treated with a mixture of 1% bovine serum albumin and 0.1% Triton X-100 for 30 min, and blocked with PBS containing 0.1% Triton X-100 and 3% normal goat serum at room temperature for 1 hour. The tissue section was then subjected to a reaction with pro SP-C (rabbit polyclonal, Sterologicals Co., USA) as a $1^{st}$ antibody at 1:100 dilution at 4° C. overnight. The tissue was washed with PBS, and treated with Alexa Fluor 488 goat anti-mouse (1:500, Molecular Probes, USA) as a $2^{nd}$ antibody in blocking solution for 1 hour. The resulting tissue was counter-stained with using DAPI (4'-6-diamidino-2-phenylindole, Molecular Probes, USA), mounted by using Vector shield (Vector Laboratories, USA), and observed with a confocal imaging microscopy (Bio Rad, USA). A fluorescence photo was taken with an Olympus EX41 fluorescence microscope using Olympus MaganFire camera X100 and X 400 lens.

As a result, the lung tissue of the rats in the control group, which were not administered with the mesenchymal stem cells, showed minimum background staining, but the lung tissues of the rats intratracheally administered with the mesenchymal stem cells showed many PKH-26 labeled transplanted cells having red fluorescence. Further, as a result of co-staining with a specific marker of type II pneumonocyte, one of lung parenchymal cells, labeled with green fluorescence, a part of located cells were co-stained. Therefore, the part of the transplanted mesenchymal stem cells, which were safely located in the rat lung tissue, was differentiated into lung parenchymal cells (FIG. 17).

Accordingly, it has been confirmed that the administration of the UCB-derived cells of the present invention is very effective for treating developmental and/or chronic lung diseases.

EXAMPLE 11

Evaluation of Therapeutic Effects of UCB- and Bone Marrow-derived Mesenchymal Stem Cells on Rats with Lung Diseases In order to demonstrate that UCB-derived mesenchymal stem cells according to the present invention are superior to bone marrow-derived mesenchymal stem cells in terms of the treatment of lung diseases, the inventive UCB-derived mesenchymal stem cells and conventional bone marrow-derived mesenchymal stem cells were administered in the same manner as in Example 3 to bronchopulmonary dysplasia rat models which were established by exposure to hyperoxia like in Example 2, and lung tissues were comparatively investigated. The bone marrow-derived mesenchymal stem cells were derived from bone marrow aspirate harvested from the iliac crest of donors (14-year-old women, 23-year-old men) with the consent of each of them. Each test group consisted of five rats, and representative tissue images are shown in FIG. 18.

As a result, the lung tissue of the bronchopulmonary dysplasia-induced rat (HC) showed chronic inflammatory responses accompanied by increased number of monocytes such as alveolar macrophages and lymphocytes, and fibrosis accompanied by over-proliferation of interstitial fibroblasts (see (b) of FIG. 18). However, the damage in pathology was significantly alleviated in the lung tissue of the rat administered with the UCB-derived mesenchymal stem cells (HT) (see (d) of FIG. 18), which was comparable to the lung tissue of the normal control (NC) (see (a) of FIG. 18), while the damage in pathology was insignificantly alleviated in the lung tissue of the rat administered with the bone marrow-derived mesenchymal stem cells (BT) (see (c) of FIG. 18).

This result suggests that UCB-derived mesenchymal stem cells according to the present invention are superior to bone marrow-derived mesenchymal stem cells in terms of the treatment of lung diseases.

While the invention has been described with respect to the above specific embodiments, it should be recognized that various modifications and changes may be made and also fall within the scope of the invention as defined by the claims that follow.

What is claimed is:

1. A method of treating bronchopulmonary dysplasia (BPD) in an infant or premature baby in need thereof, comprising intratracheal administration of a composition comprising a therapeutically effective amount of umbilical cord blood-derived mesenchymal stem cells (UCB-MSCs) to the infant or premature baby.

2. The method of claim 1, wherein said composition comprises $1.0 \times 10^5$ cells/ml to $1.0 \times 10^9$ cells/ml.

* * * * *

SEQUENCE LISTING

<160> NUMBER OF SEQ ID NOS: 8

<210> SEQ ID NO 1
<211> LENGTH: 25
<212> TYPE: DNA
<213> ORGANISM: Artificial Sequence
<220> FEATURE:
<223> OTHER INFORMATION: Sense primer of TNF-a

<400> SEQUENCE: 1
tactgaactt cggggtgatc ggtcc                                    25

<210> SEQ ID NO 2
<211> LENGTH: 24
<212> TYPE: DNA
<213> ORGANISM: Artificial Sequence
<220> FEATURE:
<223> OTHER INFORMATION: Antisense primer of TNF-a

<400> SEQUENCE: 2
cagccttgtc ccttgaagag aacc                                     24

<210> SEQ ID NO 3
<211> LENGTH: 22
<212> TYPE: DNA
<213> ORGANISM: Artificial Sequence
<220> FEATURE:
<223> OTHER INFORMATION: Sense primer of TGF-b

<400> SEQUENCE: 3
caactgtgga gcaacacgta ga                                       22

<210> SEQ ID NO 4
<211> LENGTH: 22
<212> TYPE: DNA
<213> ORGANISM: Artificial Sequence
<220> FEATURE:
<223> OTHER INFORMATION: Antisense primer of TGF-b

<400> SEQUENCE: 4
caacccaggt ccttcctaaa gt                                       22

<210> SEQ ID NO 5
<211> LENGTH: 22
<212> TYPE: DNA
<213> ORGANISM: Artificial Sequence
<220> FEATURE:
<223> OTHER INFORMATION: Sense primer of IL-6

<400> SEQUENCE: 5
caccaggaac gaaagtcaac tc                                       22

<210> SEQ ID NO 6
<211> LENGTH: 22
<212> TYPE: DNA
<213> ORGANISM: Artificial Sequence
<220> FEATURE:
<223> OTHER INFORMATION: Antisense primer of IL-6

<400> SEQUENCE: 6
ggaagcatcc atcatttctt tg                                       22

<210> SEQ ID NO 7
<211> LENGTH: 21
<212> TYPE: DNA
<213> ORGANISM: Artificial Sequence

```
<220> FEATURE:
<223> OTHER INFORMATION: Sense primer of GAPDH

<400> SEQUENCE: 7
ctctacccac ggcaagttca a                                               21

<210> SEQ ID NO 8
<211> LENGTH: 20
<212> TYPE: DNA
<213> ORGANISM: Artificial Sequence
<220> FEATURE:
<223> OTHER INFORMATION: Antisense primer of GAPDH

<400> SEQUENCE: 8
gggatgacct tgcccacagc                                                 20
```